(12) United States Patent
Nuotio et al.

(10) Patent No.: US 8,641,968 B2
(45) Date of Patent: Feb. 4, 2014

(54) CHEMICAL ANALYSER, METHOD FOR SAMPLE-BASED ANALYSIS, DEVICE FOR HANDLING CUVETTES, AND LOADING METHOD

(75) Inventors: Vesa Nuotio, Vantaa (FI); Ville Saarainen, Vantaa (FI); Juha Savonsalmi, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 418 days.

(21) Appl. No.: 12/993,243

(22) PCT Filed: May 27, 2009

(86) PCT No.: PCT/FI2009/050451
§ 371 (c)(1),
(2), (4) Date: Nov. 17, 2010

(87) PCT Pub. No.: WO2009/144381
PCT Pub. Date: Dec. 3, 2009

(65) Prior Publication Data
US 2011/0091986 A1  Apr. 21, 2011

(30) Foreign Application Priority Data

May 28, 2008 (FI) .................................... 20085509
Dec. 18, 2008 (FI) .................................... 20086209

(51) Int. Cl.
*G01N 21/07* (2006.01)
*G01N 21/13* (2006.01)
*B01L 7/00* (2006.01)
*B01L 9/06* (2006.01)

(52) U.S. Cl.
USPC ............. 422/64; 422/66; 422/68.1; 422/559; 422/561; 436/47; 436/164; 494/16

(58) Field of Classification Search
None
See application file for complete search history.

(56) References Cited

U.S. PATENT DOCUMENTS

| 5,096,672 | A | 3/1992 | Tervamaki et al. |
| 5,104,808 | A | 4/1992 | Laska et al. |
| 5,482,861 | A | * | 1/1996 | Clark et al. ..................... 436/48 |

(Continued)

FOREIGN PATENT DOCUMENTS

| CN | 2862039 Y | 1/2007 |
| CN | 101002099 A | 7/2007 |

(Continued)

*Primary Examiner* — Yelena G. Gakh
*Assistant Examiner* — Michelle Adams
(74) *Attorney, Agent, or Firm* — Birch, Stewart, Kolasch & Birch, LLP (57) ABSTRACT

A chemical analyzer, a method for sample-based analysis, a device for handling cuvette assemblies including a rotatable incubator with at least one curved opening for receiving a new cuvette assembly, an analyzer arranged around the incubator for analyzing contents of the new cuvette assembly, and a loading device adapted to carry the new cuvette assembly while initially being aligned in a straight manner before being loaded. The loading device includes a feed funnel having a first end for receiving the new cuvette assembly initially aligned in the straight manner into the feed funnel, and a second end for feeding the new cuvette assembly into the at least one curved opening, the second end having a curvature which corresponds to the curvature of the curved opening, the second end for bending the initially straight new cuvette assembly and fitting the new cuvette assembly into the at least one curved opening.

24 Claims, 4 Drawing Sheets

(56) References Cited

U.S. PATENT DOCUMENTS

| | | |
|---|---|---|
| 5,538,493 A | 7/1996 | Gerken et al. |
| 5,720,406 A | 2/1998 | Fassbind et al. |
| 5,902,548 A | 5/1999 | Watts et al. |
| 6,190,617 B1 * | 2/2001 | Clark et al. .................. 422/562 |
| 2008/0031776 A1 | 2/2008 | Sevigny et al. |

FOREIGN PATENT DOCUMENTS

| | | |
|---|---|---|
| EP | 0577822 B1 | 12/1996 |
| GB | 2036364 A | 6/1980 |
| JP | H07-505476 A | 6/1995 |
| WO | WO 93/15408 A1 | 8/1993 |

* cited by examiner

CHEMICAL ANALYSER, METHOD FOR SAMPLE-BASED ANALYSIS, DEVICE FOR HANDLING CUVETTES, AND LOADING METHOD

CROSS-REFERENCE TO RELATED APPLICATION

The present application claims priority under 35 U.S.C. §119 to PCT Patent Application No. PCT/FI2009/050451, filed May 27, 2009, Finnish Patent Application FI 2008-6209 filed Dec. 18, 2008, and Finnish Patent Application FI 2008-85509 filed May 26, 2008.

BACKGROUND OF THE INVENTION

1. Field of the Invention

The present invention relates to automatic devices and methods intended for chemical analyses. In particular, the invention relates to the analysis in automatic analysers of solutions formed by samples and reagent substances.

2. Description of Background Art

Samples have traditionally been examined using analysers, which have changed from manually operated test devices to automated multi-purpose devices. Present analysers can perform several different tests and can be used to achieve comparatively short throughput times, as well as good productivity with low personnel costs. In conventional automatic analysers, a circular rotatable incubator is traditionally used, on the outer circumference of which openings are made to receive cuvettes. The cuvettes placed in the incubators are usually reaction vessels, into which the analyser doses the substance to be analysed and the reagent substances causing reactions.

A move has taken place from the individual reaction vessels of traditional incubators to cuvettes, which contain several reaction vessels, which has increased the efficiency of analysers. For example, publication U.S. Pat. No. 5,104,808 A discloses an automatic incubator having curvaceous openings, to at least one of which has a cluster for reaction vessels, from which cluster the sample can be analysed optically after it has been mixed with reagent substances. Reaction vessels having elastic bindings, on the other hand, are known from publication U.S. Pat. No. 5,720,406 A, which discloses a principle of bending reaction vessels to curvaceous openings without analysing the samples while in a reaction vessel. Furthermore, publication EP 0577822 B1 discloses a method of cutting a portion, having at least two cuvettes, of an elastic cuvette belt and transporting the portion to openings on the perimeter of a rotatable carousel. Publication U.S. Pat. No. 5,096,672 A also discloses a cuvette row having a plurality of cuvettes, which cuvette row can be shaped in a curved form.

A problem with the type of device described has been the low degree of modularity of the analysers and the cuvettes they use. In analysers designed for present systems for large numbers of analyses, there are large incubators, into which a significant number of cuvette assemblies can be loaded. However, these cuvette assemblies cannot be utilized in analysers intended for smaller numbers of samples, so that a special type of cuvette assembly is required for each size of device, which leads to additional purchase and storage costs.

SUMMARY AND OBJECTS OF THE INVENTION

The present invention is intended to eliminate at least some of the defects of the prior art and for this purpose create a chemical analyser and analysis method, in connection with which it is possible to use standardized bendable cuvette assemblies, which can receive several samples.

The chemical analyser according to the invention comprises a rotatable incubator, which is equipped with openings to receive the cuvettes loaded into it. In the analyser, there are, in addition, analysis means arranged around the incubator and a loading device for loading the cuvette assemblies into the openings, which are curved. For its part, the analyser-loading device comprises a feed funnel, by means of which a straight cuvette assembly is bent to fit into the curved openings of the incubator, and a ram, by means of which the cuvette assemblies are loaded into the openings of the incubator, through the feed funnel.

In the method according to the invention for analysing samples, the analysis sequence is defined sample-specifically, after which a cuvette assembly, which comprises at least two reaction vessels, into which the sample and the reagent are dosed, is loaded into an opening in the incubator through a bending feed funnel, which bends the cuvette assembly to fit said opening. In the analysis of the sample, at least one sample in the cuvette assembly is analysed, the sample being in a reaction vessel.

The device according to the invention for handling cuvettes comprises a rotatable incubator and a loading device. In the incubator, there is at least one curved opening for receiving and transporting a cuvette assembly. The loading device comprises a loading track for storing unloaded straight cuvette assemblies and transporting them to the incubator, as well as a ram, which is arranged to press the cuvette assembly at the incubator end of the loading track into an opening in the incubator. The loading device also comprises a feed funnel, which is arranged to receive the straight cuvette assembly pressed by the ram and to bend it to allow it to be pushed into the curved opening of the incubator.

In the loading method according to the invention for loading a cuvette assembly into an opening in an incubator, the cuvette assembly is transported to the location of the opening in the incubator and loading into the opening in the incubator by moving the ram. During loading, the cuvette assembly is shaped to fit the opening in the incubator by using the ram to load it through the curved feed funnel.

Considerable advantages are gained with the aid of the invention. Thanks to the feed funnel of the analyser, analysers of different sizes can use same-size standard cuvettes, which contain several sample vessels. Analysers suitable for standardized cuvette assemblies receiving many samples permit volume benefits when purchasing cuvettes. The storage of the cuvettes too is cheap, as only one type of cuvette assembly is required, so that additional resources are not needed to maintain the articles. In addition, because the cuvette assembly is straight, it is easier to store than, for example, a curved cuvette assembly.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, embodiments of the invention are examined in greater detail with reference to the accompanying drawings.

DETAILED DESCRIPTION OF THE PREFERRED EMBODIMENTS

Figure 1:
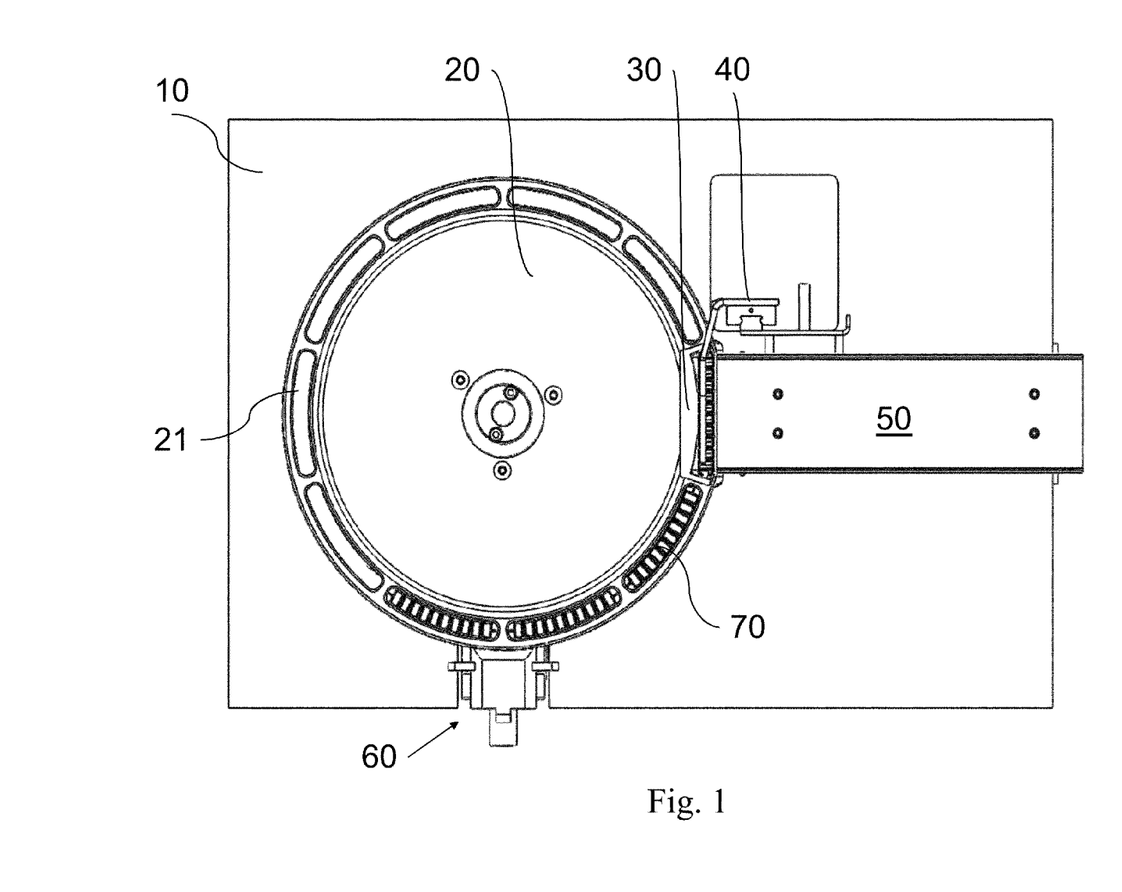
FIG. 1 shows a top view of the analyser according to the invention.
Figure 2:
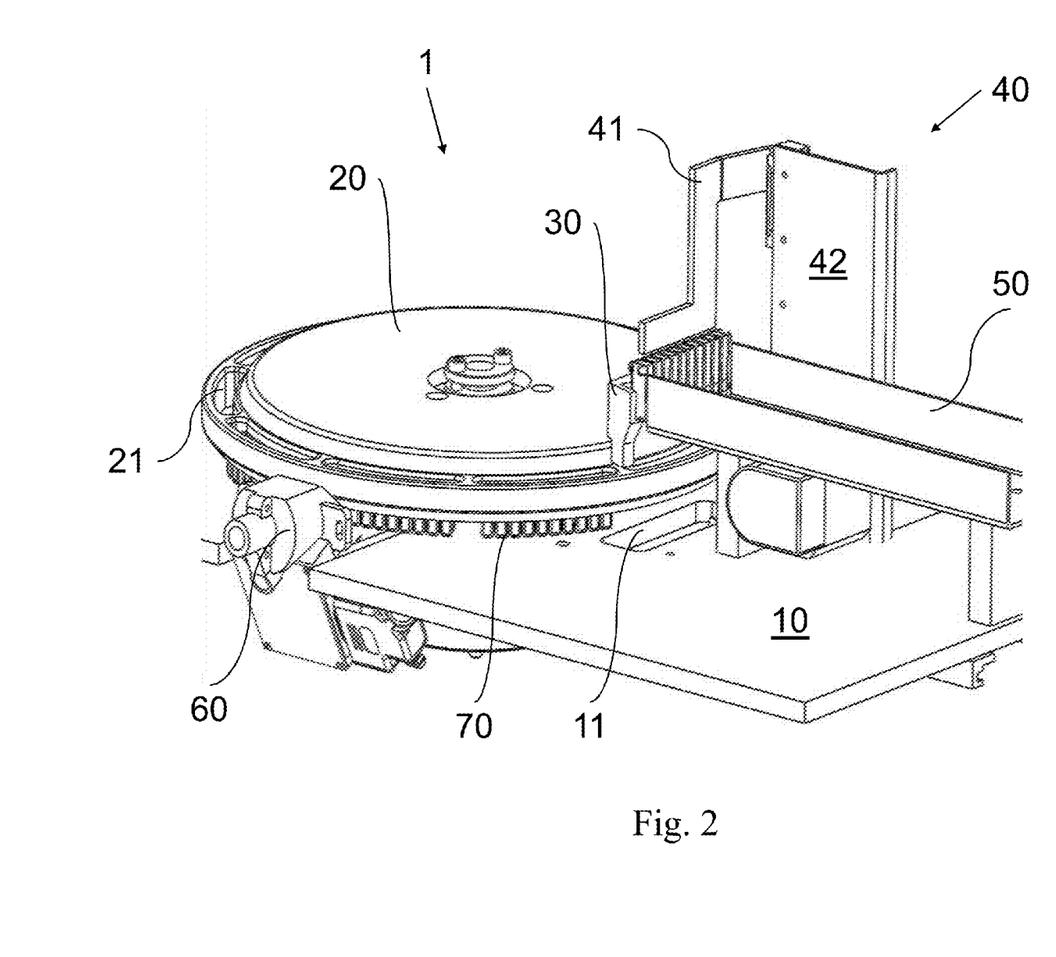
FIG. 2 shows a perspective view of the analyser of FIG. 1.

As can be seen from FIGS. 1 and 2, the analyser 1 according to the invention comprises a heated incubator 20, on the outer edge of which openings 21 are made, to receive cuvette assemblies. The incubator according to the invention is particularly suited for use with cuvette assemblies that are made from a sufficiently elastic and clear material. The elasticity permits elastic bending of the connecting web part of the cuvettes relative to its longest side, while the clearness permits the sample contained in the cuvette assembly to be analysed through the wall of the cuvette, so that it is not necessary to remove the sample from the cuvette assembly during analysis. According to the invention, a cuvette assembly 70, which consists of several reaction vessels and web parts connecting them, is loaded into the openings 21 of the incubator 20. The cuvette assembly 70 can contain, for example, 10 reaction vessels next to each other, in such a way that their connecting web parts are parallel to each other, in which case the orientation of the cuvette assembly 70 is straight and it can receive 10 different samples. The outermost reaction vessels of a particularly advantageous cuvette assembly 70 are, in addition, equipped with flexible tongues, with the aid of which the cuvette assembly 70 can be bent into a curve, without immediately compressing the outermost sample vessels. Cuvette assemblies like those described, which are especially well suited to the invention, are disclosed in Finnish patent application 20085509, now Finnish Patent No. FI 120818 issued Mar. 31, 2010.

The circular incubator 20 according to the invention is mounted on bearings in the centre and rotation means (not shown) are fitted to it, with the aid of which the incubator 20 can be rotated to the desired extent in the desired direction. The rotation means can comprise, for example, a servomotor, which has excellent positioning precision, but the price of which is extremely high. Indeed, the power transmission of the incubator 20 can be implemented with sufficient precision by fitting it directly to the shaft of a cost-effective stepped motor, which is sufficiently precise for the purpose, so that there are only the essential number of moving parts, and thus the minimum number of causes of play, in the transmission. In the power transmission of the rotation means, it is essential that the rotational speed and positioning precision are sufficiently great and that accelerations of the incubator 20 are controlled and soft.

The analyser 1 also comprises a loading device 40 fitted in connection with the incubator 20. The loading device 40 comprises means for delivering the cuvette assemblies 70 to the incubator 20. The loading device 40 comprises a loading track 50, along which the cuvette assemblies 70 are brought for loading into the opening 21 of the incubator 20. At its simplest, the loading track 50 is a trough with a U-shaped cross-section, the bottom of which is dimensioned to be as wide as the lower edge of the cuvette assembly 70 being loaded and that the vertical edges of the trough are essentially higher than the cuvette assembly 70. Thus, the cuvette assembly 70 can be transported on the loading track 50 from its lugs, in such a way that the lugs of the cuvette assembly 70 are set on top of the vertical edges of the loading track 50, thus keeping the lower edges of the sample vessel at a distance from the bottom of the loading track 50. The gap remaining between the lower edge of the cuvette assembly 70 and the bottom of the loading track 50 ensures that the lower edge of the cuvette assembly 70 does not drag along the bottom of the loading track 50, and thus does not cause noise or scratching. Because the cuvette assemblies 70 transported on the loading track 50 are straight, their transportation is easy and they will not easily jam when being pushed. The cuvette assemblies 70 are transported by a pusher (not shown), which pushes a row of cuvette assemblies 70 suspended by their lugs forwards to the incubator 20. The pusher can be, for example, a simple pneumatic cylinder, which can be controlled by remote commands. Alternatively, the loading track 50 can be sloping, in which case the cuvette assemblies 70 move along the track by gravitational acceleration, so that there will always be a cuvette assembly 70 at the feed funnel 30, ready to be loaded. However, more than one cuvette assembly 70 cannot be in the feed funnel 30 at one time, because the shaft of the ram (cuvette manipulator) 41 prevents the next cuvette assembly 70 from entering the funnel during the loading movement.

The feed funnel 30, which is part of the loading device 40 and through which the cuvette assemblies 70 are fed to the openings 21 of the incubator, is fitted to the end of the loading track 50 next to the incubator 20. In loading, the ram 41 of the loading device 40 is used, the lower edge of which is arranged to press the cuvette assembly 70 with a single movement into the feed funnel 30, in which it is arranged to be shaped to fit the opening 21. The curvature of the opening 21 conforms to the curvature of the outer circumference of incubator 20. Due to the flexibility of the cuvette assembly 70, it can be used for incubators 20 of several different sizes, which have different radii of curvature. In this connection, the term straight refers to a cuvette, the curvature of which has not been changed by bending the cuvette. Correspondingly, the term a curved cuvette assembly refers to a cuvette assembly, the curvature of which has been changed by bending the cuvette assembly.

Figure 3:
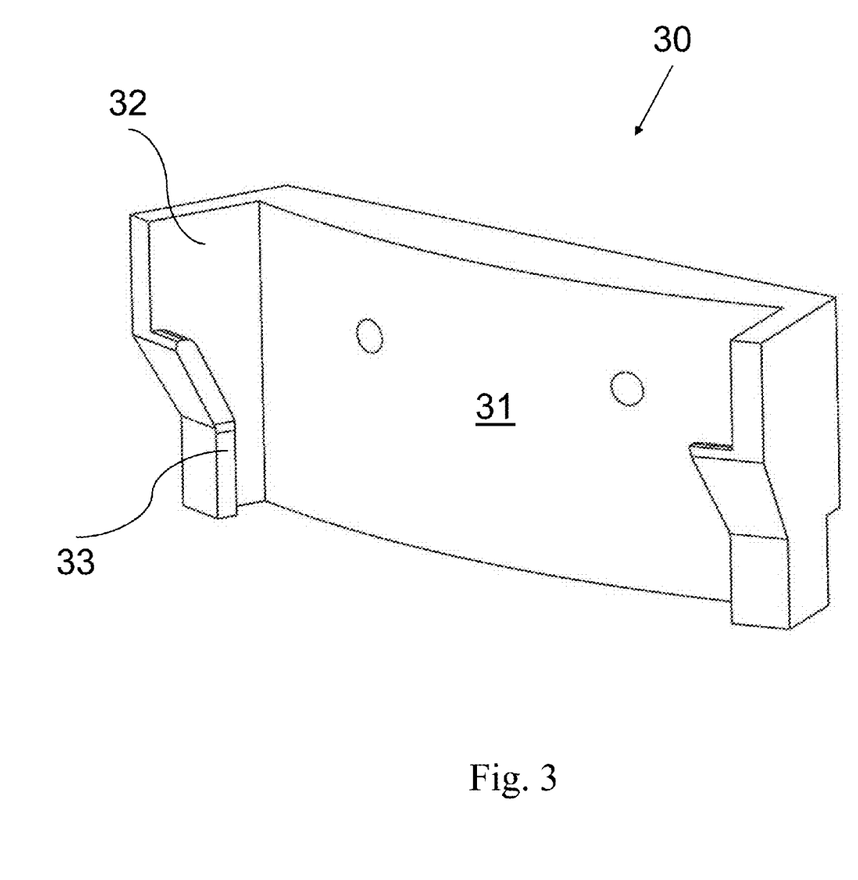
FIG. 3 shows the feed funnel of FIGS. 1 and 2.

As can be seen from FIG. 3, the feed funnel 30 is shaped in such a way that when travelling through it, a cuvette assembly 70 takes a curved shape suitable for the opening 21, by means of a single movement of the ram 41. The side 31 of the feed funnel 30 receiving the cuvette assembly 70 is convex, when examined from the direction of arrival of the cuvette assembly 70, so that, when pressed against it, the cuvette assembly 70 bends to conform to the circumference of the incubator 20. The feed funnel 30 is dimensioned in such a way that the curvature of its lower edge corresponds to the curvature of the openings 21 in the incubator 20. In other words, it is possible to manufacture different types of feed funnel 30, which suit incubators 20 of different sizes, in which, however, the same type of cuvette assembly 70 can be used, which leads to the cost benefits sought by the invention. Because the cuvette assemblies 70 used in the analyser 1 are straight when not in use, they are economical to store.

The curvature of the side 31 of the loading device 40 receiving the feed funnel 30 can be flat, i.e. constant, or can vary in the vertical direction, in which case the receiving side 31 is planar on its upper edge and curves more steeply convexly when examined downwards. In that case, the cuvette assembly 70 is arranged to bend in stages according to the receiving side 31, whereas, when the side 31 is evenly curved, the cuvette assembly 70 is arranged to bend immediately into the desired curve. The feed funnel 30 is also equipped with lugs on the receiving side edges, which guide the cuvette assembly laterally. Thus, the cuvette assembly 70 is firmly in contact through only the lugs, so that they take the wear and scratching caused by bending. Thus, the delicate surfaces of the cuvette assembly 70 are protected from wear. In addition, the side edges of the feed funnel are equipped which guides 33, which bend the cuvette assembly into a curve. When the cuvette assembly 70 is pressed onto the lower edge of the feed funnel 30, its lugs are pressed inwards and its partitions are bent, so that the cuvette assembly 70 lies tightly against the receiving side 31 of the feed funnel 30 and is ready to be loaded as tightly into the opening 21 of the incubator 20. With the aid of the lugs, the cuvette assembly 70 is positioned and centres itself into the opening 21 of the incubator 20, even though the incubator 20 may not be in precisely the correct position.

The loading device 40 comprises a vertical guide post 42, to the outer edge of which the vertically moving ram (cuvette manipulator) 41 is fitted. The ram 41 can be moved, for example, by means of a vertical linear drive, or an electric motor, to the shaft of which a toothed belt is fitted. The movement of the ram 41 is long enough that, when it presses the cuvette assembly 70 downwards, its upper edge is pressed into the opening 21 at the desired height. The vertical positioning is thus defined according to the press depth of the ram 41, which press depth can preferably be adjusted to be suitably programmatically, for example, by limiting the angle of rotation of the electric motor. As above, when loading the cuvette assembly 70 into the opening 21, its lugs take most of the wear, from which its other surfaces are protected. After the successful loading of the cuvette assembly 70 pressed into the opening 21 in the incubator 20, the sample to be analysed, or the reagent substance is dosed into it.

The incubator 20 is heated by electric resistances. There can also be thermal insulation around the incubator, in order to stabilize the temperature. The heating is intended to maintain the most favourable analysis conditions, due to which heat is conducted to the sample vessels of the cuvette assembly 70 and from there to the samples that they contain. For example, when analysing human samples, the target temperature can be 37° C. However, when using cuvette assemblies 70 of the type described above, due to the partitions and lugs they contain, the reaction vessels are separated from each other and from the ends of the openings 21, so that temperature distortions between the sample vessels are avoided. Alternatively, the incubator 20 can also be cooled to a target temperature, if the prevailing temperature is too high. Cooling can be implemented using, for example, a Peltier element.

The analysis means 60 are arranged around the incubator 20, so that the cuvette assemblies 70 need not be removed from the opening 21 during the test. For example, according to one preferred embodiment, the lower part of the cuvette assembly 70 is manufactured from a clear and transparent material, through which optical tests can be performed directly, without removing the cuvette assembly 70 from the opening 21. Thus, the recesses of the cuvette assembly 70 loaded into an opening 21 of the incubator 20 from the loading track 50 are arranged to receive substances from several manipulators, simply by altering the position of the incubator 20. The analysis procedure can then be arranged, for example, in such a way that the reagent is dosed into the reaction vessel of the cuvette assembly 70 using a reagent doser, which takes the substance from a reagent store. The reagent store and doser too are arranged around the incubator 20. Dosing of a reagent requires the incubator 20 to be rotated to the correct position, so that the correct reaction vessel of the correct cuvette assembly 70 will be at the reagent reception position. The basic idea of the arrangement is indeed that the sample is moved in the cuvette assembly 70 that has received it, the position of which is altered by rotating the incubator 20, so that movements and directions of movement in the analyser 1 will be as few as possible. The analysis means 60 can also comprise an analysis device, which sucks the sample from the reaction vessel of the cuvette assembly 70 and measures its properties inside the device. A conventional analysis device like that described can be, for example, an ion-selective electrode. The samples are analysed using an optical analysis method, for instance, photometrically.

The samples to be analysed are dosed under the same conditions as the reagent substances using a sample doser, which takes the substance from a sample store. The dosing sequence of sample and reagent substance can vary in a manner required by the tests in the analysis. The sample and reagent stores are usually carousel-type indexed stores, the storage locations and positions of which are controlled by remote control as part of the control of the entire analyser 1. The reagent and sample can be mixed by rotating the incubator 20 into the vicinity of a separate mixer and starting the mixer. The content of each reaction vessel can be analysed optically as described above and, for example, by using a manipulating analyser, which is arranged to suck the sample into its test chamber and measure its voltage compared to a reference value. The setting and programming of the test periods and movements is known. There is at least one analysis station. The number and locations of the analysis devices is limited by the number of stations that will fit around the incubator.

In the method according to the invention, an apparatus like that described above is used by sample analysis, in which the analysis event is controlled sample-specifically. A sample-specific and based test sequence is based on an analyser construction that permits the flexible arrangement of the periods of the test to be performed, in such a way that the tests required by each sample can be run one after the other as required. The said flexibility is based on the analysis means, substance stores, and mixers arranged around a rotatable incubator. The reaction vessel transporting the sample is then not bound to a specific path, but can be moved to a desired station as required.

Figure 4:
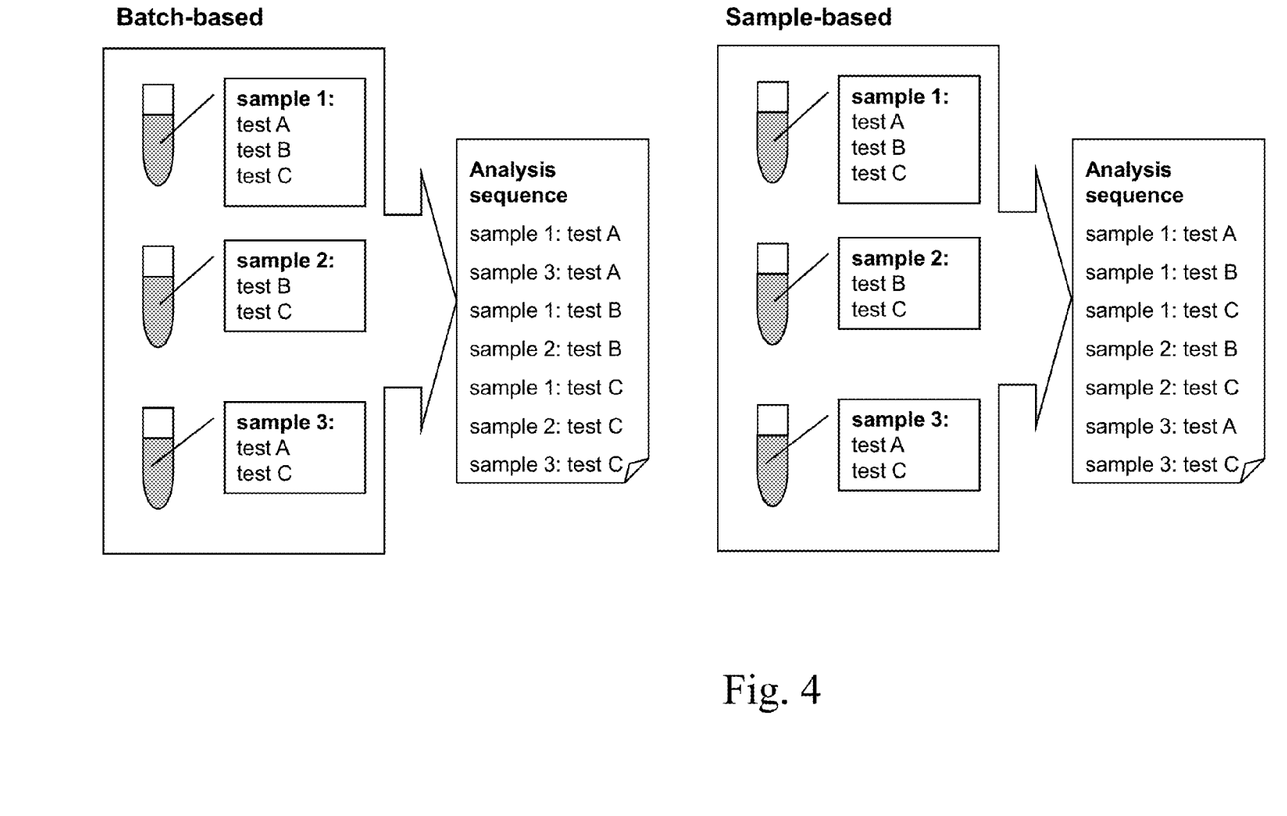
FIG. 4 shows the difference between sample-based and test-batch-based analysis.

Thus, a sample is dosed into the analyser's 1 reaction vessel, where it remains only for the time required for dosing, incubation, and mixing. The difference between sample and test-based analysis is shown in FIG. 4. Sample-based analysis leads to a short through-put time and a possibility to change the test sequence flexibly. The changing of the test sequence allows, for example, an urgent test to be prioritized to be made before the analysis of the other samples, without having to wait for the right types of test.

Once the tests for all of the sample vessels used in the cuvette assembly 70 are ready, the cuvette assembly 70 can be removed from the opening 21, in such a way that the ram 41 that performed loading pushes the cuvette assembly 70 out of the opening 21 into a separate receiving trash container, or an exit opening 11 in the frame 10. Alternatively, the ram 41 can load a new cuvette assembly 70 into the feed funnel 30 through the opening 21, in which case the used cuvette assembly 70 is pushed by a new cuvette assembly to fall into a separate trash container, or an exit opening 11 in the frame 10. Alternatively, the analyser 1 can be constructed in such a way that the cuvette assemblies 70 are loaded into the openings 21 from below, in which case the loading device 40 with the feed funnel 30 would be arranged beneath the incubator 20. In that case, however, it would be more difficult to remove the cuvette assemblies 70 from the openings 21, due to which it is not a preferred embodiment of the invention.

In order to ensure a short throughput time and high productivity, the analyser 1 according to the invention is also, according to one preferred embodiment, equipped with at least one incubator 20, one reagent store and one sample store, as well as their dosers or combinations of them, one mixer, and one optical analysis means 60. Thus, during a single test period, several operations can be performed simultaneously on different samples. According to one embodiment, for example during an eight-second period, one sample and one reagent substance can be dosed, two mixtures can be mixed, and five samples can be analysed.

TABLE 1

Reference numbers

| Reference number | Component |
| --- | --- |
| 10 | frame |
| 11 | exit opening |
| 20 | incubator |
| 21 | opening |
| 30 | feed funnel |
| 31 | surface receiving the cuvette |
| 32 | side edge |
| 33 | guide |
| 40 | loading device |
| 41 | ram |
| 42 | guide post |
| 50 | loading track |
| 60 | analysis means |
| 70 | cuvette |

The invention claimed is:

1. A device for handling cuvette assemblies, comprising:
a recipient structure having at least one curved opening that has a curvature and is configured to receive and transport a new cuvette assembly, and
a loading device adapted to carry the new cuvette assembly while the new cuvette assembly is initially aligned in a straight manner and before the new cuvette assembly is loaded into the recipient structure,
wherein the loading device comprises a feed funnel having:
a first end adapted to receive the new cuvette assembly initially aligned in the straight manner into the feed funnel, and
a second end for feeding the new cuvette assembly into said at least one curved opening of the recipient structure,
the second end having a curvature which corresponds to the curvature of said at least one curved opening of the recipient structure, the second end being adapted to bend the new cuvette assembly that is initially aligned in the straight manner in order to fit the new cuvette assembly into said at least one curved opening of the recipient structure.

2. The device for handling cuvette assemblies according to claim 1, wherein the loading device comprises a ram which is configured to load the new cuvette assembly through said feed funnel and into said at least one curved opening of the recipient structure.

3. The device for handling cuvette assemblies according to claim 2, wherein the ram is configured to push the new cuvette assembly through the feed funnel in a single movement.

4. The device for handling cuvette assemblies according to claim 2, wherein the ram of the loading device is configured to push a previously used cuvette assembly out of said at least one curved opening.

5. The device for handling cuvette assemblies according to claim 2, wherein the ram is configured to push a previously used cuvette assembly out of said at least one curved opening by having the new cuvette assembly displace the previously used cuvette assembly out from said at least one curved opening of the recipient structure.

6. The device for handling cuvette assemblies according to claim 2, wherein the feed funnel is fitted between the ram and said at least one curved opening.

7. The device for handling cuvette assemblies according to claim 1, wherein the loading device comprises a loading track that carries multiples of the new cuvette assembly, before each of the multiples of the new cuvette assembly is loaded into the recipient structure.

8. The device for handling cuvette assemblies according to claim 7, wherein the loading track has a U-shaped cross-section.

9. The device for handling cuvette assemblies according to claim 1, wherein the feed funnel comprises an evenly curved cuvette assembly contacting surface for receiving the new cuvette assembly, wherein a curvature of the cuvette assembly contacting surface at the second end corresponds to the curvature of said at least one curved opening of the recipient structure.

10. The device for handling cuvette assemblies according to claim 1, wherein the feed funnel comprises a cuvette contacting surface for receiving the new cuvette assembly,
wherein the cuvette contacting surface varies in a vertical direction of the feed funnel by gradually curving more steeply and convexly direction along a beginning from the first end and continuing to the second end of the feed funnel, the cuvette contacting surface varying in such a way that the cuvette contacting surface at the second end of the feed funnel corresponds to the curvature of said at least one curved opening of the recipient structure.

11. A chemical analyzer which comprises:
a rotatable incubator comprising at least one curved opening for receiving a new cuvette assembly,
an analysis means analyzer arranged around the incubator for analyzing contents of the new cuvette assembly in the at least one curved opening of the incubator, and
a loading device adapted to carry the new cuvette assembly while the new cuvette assembly is initially aligned in a straight manner and before the new cuvette assembly is loaded into the incubator,
wherein the loading device comprises a feed funnel having:
a first end adapted to receive the new cuvette assembly initially aligned in the straight manner into the feed funnel, and
a second end for feeding the new cuvette assembly into said at least one curved opening of the incubator,
the second end having a curvature which corresponds to a curvature of said at least one curved opening of the incubator, the second end being adapted to bend the new cuvette assembly that is initially aligned in the straight manner in order to fit the new cuvette assembly into said at least one curved opening of the incubator.

12. The chemical analyzer according to claim 11, wherein the analyzer is arranged to analyze samples when the samples are in the new cuvette assembly.

13. The chemical analyzer according to claim 11, wherein the analyzer further comprises a sample doser for dosing samples into sample vessels of the new cuvette assembly.

14. The chemical analyzer according to claim 11, wherein the analyzer further comprises a reagent doser for dosing a reagent into the new cuvette assembly and a reagent store which is at most at a distance of an operating reach of the reagent doser from the incubator.

15. The chemical analyzer according to claim 11, wherein the analyzer further comprises a sample store which is at most at a distance of an operating reach of the sample doser from the incubator.

16. The chemical analyzer according to claim 11, wherein the loading device comprises a ram which is configured to load the new cuvette assembly into said feed funnel and then into said at least one curved opening of the incubator.

17. The chemical analyzer according to claim 16, wherein the ram is configured to push the new cuvette assembly through the feed funnel in a single movement.

18. The chemical analyzer according to claim 16, wherein the ram of the loading device is configured to push a previously used cuvette assembly out of said at least one curved opening of the incubator.

19. The chemical analyzer according to claim 16, wherein the ram is configured to push a previously used cuvette assembly out of said at least one curved opening by having the new cuvette assembly displace the previously used cuvette assembly out from said at least one curved opening of the incubator.

20. The chemical analyzer according to claim 16, wherein the feed funnel is fitted between the ram and said at least one curved opening of the incubator.

21. The chemical analyzer according to claim 11, wherein the loading device comprises a loading track that carries multiples of the new cuvette assembly, before each of the multiples of the new cuvette assembly is loaded into the incubator.

22. The chemical analyzer according to claim 21, wherein the loading track has a U-shaped cross-section.

23. The chemical analyzer according to claim 11, wherein the feed funnel comprises an evenly curved cuvette assembly contacting surface for receiving the new cuvette assembly, wherein a curvature of the cuvette assembly contacting surface at the second end corresponds to the curvature of said at least one curved opening of the incubator.

24. The chemical analyzer according to claim 11, wherein the feed funnel comprises a cuvette contacting surface for receiving the new cuvette assembly,
   wherein the cuvette contacting surface varies in a vertical direction of the feed funnel by gradually curving more steeply and convexly direction along a beginning at the first end and continuing to the second end of the feed funnel, the cuvette contacting surface varying in such a way that the cuvette contacting surface at the second end of the feed funnel corresponds to the curvature of said at least one curved opening of the incubator.

\* \* \* \* \*